United States Patent [19]

Mori

[11] Patent Number: 4,657,350

[45] Date of Patent: Apr. 14, 1987

[54] PROCESS FOR MANUFACTURING A DOUBLE REFRACTION PLATE

[75] Inventor: Toshio Mori, Yokohama, Japan

[73] Assignee: Sony Corporation, Tokyo, Japan

[21] Appl. No.: 830,242

[22] Filed: Feb. 18, 1986

Related U.S. Application Data

[63] Continuation of Ser. No. 530,609, Sep. 9, 1983, abandoned.

[30] Foreign Application Priority Data

Sep. 14, 1982 [JP] Japan ................................. 57-158808

[51] Int. Cl.$^4$ ............................ G02B 5/30; B05D 5/06
[52] U.S. Cl. .................................... 350/400; 350/401; 427/105; 427/163; 427/164; 427/166; 427/167; 427/248.1; 427/255
[58] Field of Search ............... 427/163, 164, 166, 167, 427/10, 248.1, 255; 350/165, 411, 339 R, 400, 401

[56] References Cited

U.S. PATENT DOCUMENTS

| | | | |
|---|---|---|---|
| 2,973,686 | 3/1961 | Dreytus et al. | 118/715 X |
| 3,698,946 | 10/1972 | Kaspaul et al. | 427/10 |
| 3,834,792 | 9/1974 | Janning | 428/1 |
| 4,024,291 | 5/1977 | Wilmanns | 427/10 |
| 4,150,877 | 4/1979 | Kobale et al. | 350/339 R |
| 4,248,502 | 2/1981 | Bechteler et al. | 350/164 |

*Primary Examiner*—Richard Bueker

[57] ABSTRACT

A novel process for producing a double refraction plate is disclosed. According to the process, a transparent dielectric material is directed to and deposited on a substrate from an oblique direction. Above all, for controlling the retardation of the resulting double refraction plate, a polarized light having a plane of polarization in a specific direction relative to the substrate is directed to the substrate through the variable phase plate and the light reflected from the substrate is observed through the variable phase plate, as the dielectric material is deposited from an oblique direction.

13 Claims, 5 Drawing Figures

TO VACUUM PUMP (A)

(B)

PROCESS FOR MANUFACTURING A DOUBLE REFRACTION PLATE

This is a continuation of application Ser. No. 530,609, filed Sept. 9, 1983, now abandoned.

BACKGROUND OF THE INVENTION

1. Field of the Invention

This invention relates to a process for manufacturing a double refraction plate used for various optical devices and more particularly to a novel process for manufacturing a double refraction plate according to which a transparent or light transmitting material such as metal oxide is deposited on a substrate from an oblique direction relative to the substrate surface.

2. Description of the Prior Art

A light arriving at a certain crystal or at an isotropic material placed in an electric field is refracted in two directions. This phenomenon is known as birefringence or double refraction, said crystal or the material having two discrete indices of refraction. This phenomenon is related with atomic orientation of the material or crystal and is caused by anisotropy proper of the material or crystal, that is, the characteristics of the physical properties thereof such as the rate of thermal expansion, electrical conductivity or thermal conductivity are varied with the direction in which the measurement of these properties is made. The light incident on the crystal plate showing these characteristics is split in two light wave components oscillating in two mutually perpendicular directions. In case the crystal plate is a uniaxial crystal, one of the light components is refracted in the usual manner of refraction through an isotropic medium. However, the refraction of the outer light component apparently does not obey the rule of refraction. Thus the index of refraction is varied with the direction of the plane of polarization. This difference in the index of refraction means that the speed of the light beam is varied with the direction in which it is proceeding.

Double refraction plates having the aforementioned characteristics are used in many optical components or devices making use of the anisotropic properties thereof with respect to light beams. Typical of them are wave plates or polarizers enclosed in an optical pickup for optical video disk units or an optical low-pass filter used in various image pickup devices. Above all, wave plates such as a quarter plate (¼-wave plate) or an octant plate (⅛-wave plate) are formed by double refraction plates having the desired value of retardation and are used for modulating the plane of polarization as desired. By retardation is meant the optical path difference between two linearly polarized light components oscillating in mutually perpendicular directions.

Typical of the aforementioned crystals exhibiting double refraction are quartz and calcite. Thus the wave plates or polarizers are usually manufactured by cutting and polishing (grinding) the quarz for reducing their thickness. However, in this case, the polishing operation of the quartz or calcite must be performed with great accuracy, thus raising manufacturing costs. Moreover, because of limitation in size of the quartz or calcite, the resulting double refraction plate is also limited in size, thus making it impossible to manufacture a product of a larger size.

In place of the double refraction plate of quartz or the like, materials which are limited in size and expensive as mentioned above, it is also known to produce a double refraction plate by tensilizing a polymer film for providing an appropriate molecular orientation. With this process, the polymer film is tensilized in a certain direction for orienting and crystallizing the molecules of the polymer film in a specific direction for providing anisotropic properties of the crystal similar to those of quartz or calcite. In this manner, it has been possible to manufacture a double refraction plate having a larger size at lower costs. However, the double refraction plate with the desired retardation is extremely difficult to manufacture from the polymer film with improved accuracy.

SUMMARY OF THE INVENTION

The present invention has been made for obviating the drawback inherent in the aforementioned prior-art device and has as an object to provide a novel process for facilitating the manufacture of a double refraction plate.

It is a further object of the present invention to provide a process for manufacturing a double refraction plate at reduced costs.

It is a further object of the present invention to provide a process for manufacturing double refraction plates according to which the retardation of the resulting refraction plates can be controlled as desired.

The present inventors have found by perseverent research and tests that a deposited film of dielectric material obtained by depositing the material on the surface of a glass or metal substrate from an oblique direction relative to said surface exhibits birefringent characteristics desired.

These and other objects and features of the present invention will be apparent from the following part of the specification which indicate preferred embodiments of the present invention.

DESCRIPTION OF THE PREFERRED EMBODIMENTS

Figure 1:
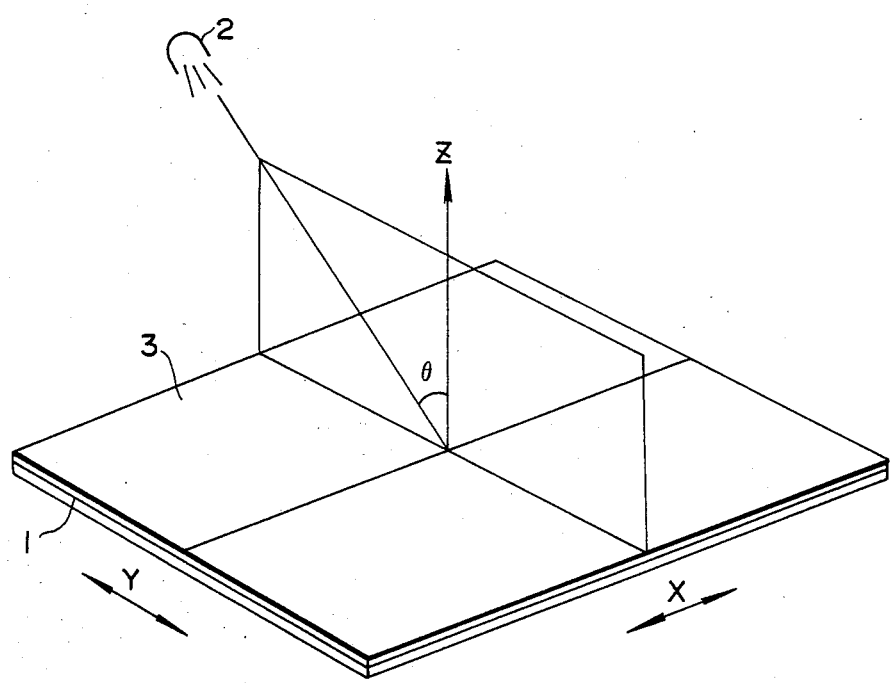
FIG. 1 is a schematic perspective view showing a double refraction plate obtained in accordance with the present invention.

According to the present invention, a dielectric material 2 is vapor-deposited on a substrate 1 at an incident angle $\theta$ as shown in FIG. 1 for providing a deposited film 3. The refractive index of the resulting film is higher for the light wave oscillating in the X-axis direction than in the Y-axis direction. In this case, the light passing through the deposited film is split into a linear component oscillating in the X-axis direction with the lowest phase velocity and a linear wave component oscillating in the Y-axis direction perpendicular to the X-axis direction with the highest phase velocity. The optical path difference between the two linear components is known as a retardation $\Gamma$, and given by a formula $$\Gamma = (n_X - n_Y)d \tag{1}$$

where $n_X$, $n_Y$ denote a refractive indices for linear components oscillating in the X and Y directions, respectively and d denotes thickness of the birefringent medium, that is, thickness of the deposited film 3.

Figure 2:
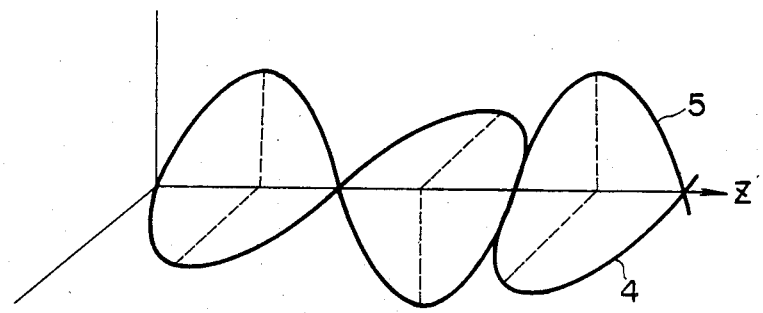
FIGS. 2A, 2B are charts showing the manner in which the retardation is caused.
Figure 2:
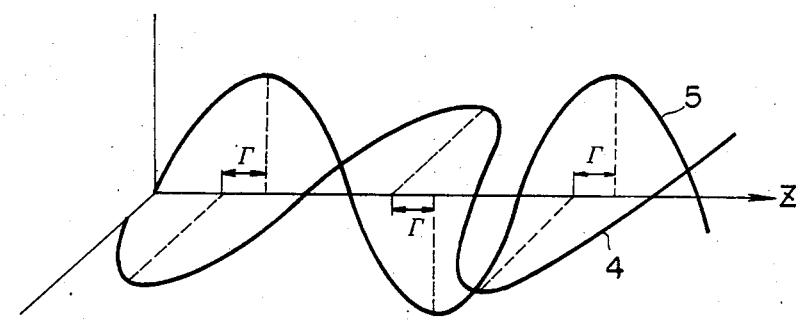

Reference is now made to FIGS. 2A and 2B for describing this retardation $\Gamma$. Before the light is passed through the deposited film 3, the phase of a linear component 4 in the X-axis direction is coincident with that of a linear component 5 in the Y-axis direction. However, once the light has passed through the deposited film 3, a deviation is caused to exist between the phase of the linear X-axis direction component 4 and that of the linear Y-axis direction component 5, as shown in FIG. 2B. Retardation $\Gamma$ is this deviation expressed in terms of Angstroms (Å). Therefore, a double refraction plate, i.e. the deposited film 3 having a certain retardation, acts as a wave plate, such as a quarter plate or octant plate, to a light having a specific wavelength.

This effect of double refraction is probably caused by the fact that the direction of growth of the deposited particles is controlled due to the so-called self-shadow effect so that the particles can be interlinked with more difficulty in the Y-axis direction than in the X-axis direction perpendicular to the plane of incidence. Also, the interlinked particle structure is sufficiently small in size as compared to the light wavelength, and the refractive index in the X-axis direction $n_X$ is larger than that in the Y-axis direction, thus causing double refraction.

Figure 3:
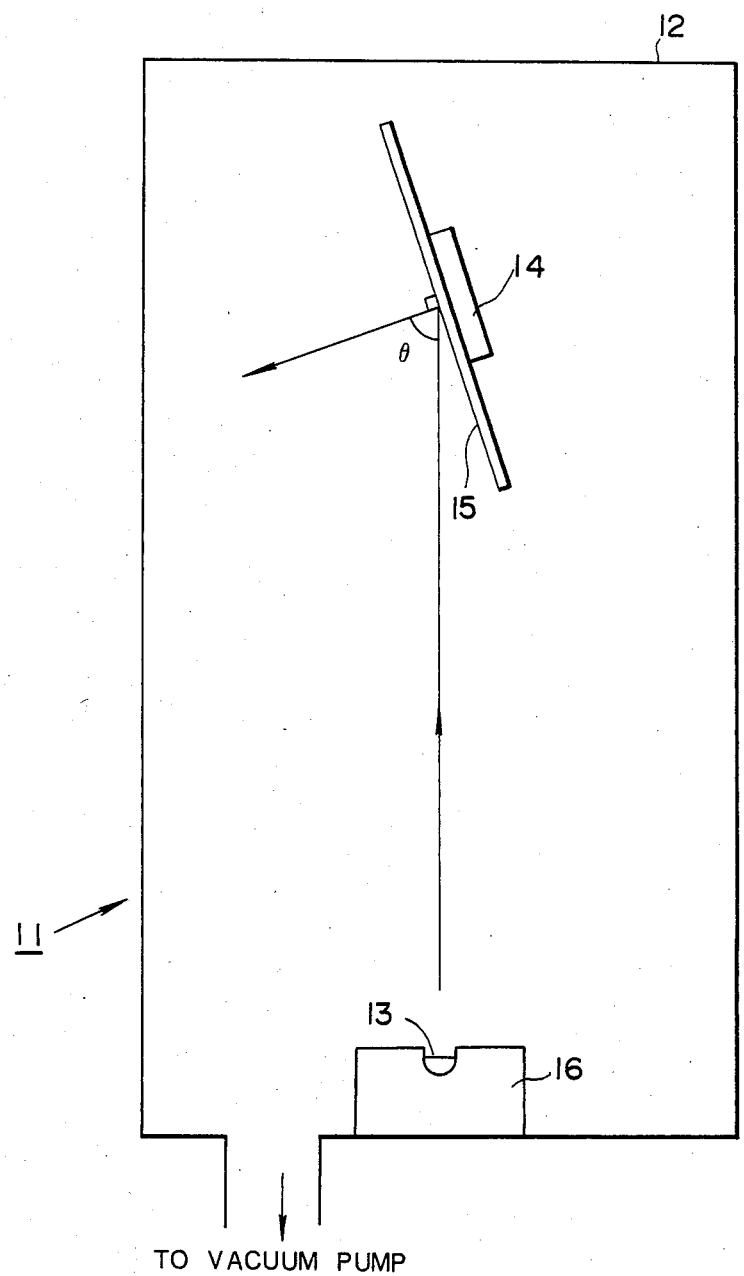
FIG. 3 is a side elevation showing a first deposition unit used in a first embodiment of the invention.

Thus the present inventors conducted a test in which a dielectric material is deposited from an oblique direction by using a first vapor-deposition unit 11 as shown in FIG. 3 and obtained data as shown in Examples 1 through 4.

While a desired effect may be obtained with the deposition incident angle larger than 30°, a practically useful double refraction plate is obtained with said angle larger than 45°. While the desired effect may be obtained with the use of metal oxides or sulfides as the deposited material from a deposition source 13, it is thought that similar effects may be obtained by using transparent materials such as polymer materials or metal nitrides or sulfides.

The double refraction plate obtained by the method described above is shown in greater detail in the following Examples 1 through 4. It should be noted that double refraction plates may be manufactured very easily with the desired shape and size by oblique deposition, that is, oblique vacuum evaporation by using the deposition unit 11. In addition, by using a second vapor-deposition unit 21 as shown in FIG. 5, double refraction plates of higher precision and desired retardation $\Gamma$ may be manufactured under visual inspection and monitoring of the deposition process.

The present invention will be described further by referring to several Examples. However, it is to be understood that these examples are intended to illustrate the invention and are not to be construed to limit the scope of the invention.

EXAMPLE 1

With the use of the first deposition unit 11, titanium oxide ($TiO_2$) as deposition source 13 was heated locally by an electron beam used as heating means 16, for depositing the material.

As shown in FIG. 3, this first deposition unit 11 is made up of a bell jar 12 in which a vacuum is maintained by a vacuum pump, not shown, a deposition source 13 for depositing various materials, and a base plate mounting unit 14 orientable to any desired angle relative to the direction of the vapor produced from the deposition source 13. The heating unit 16 is provided for the deposition source 13 for vaporizing various materials. The heating unit 16 may be a resistance heating unit or an electron beam, laser beam or infrared rays for locally heating the source 13, depending on the kind of source 13 employed. The air in the bell jar 12 is exhausted by a vacuum pump, not shown, whereby a vacuum less than $10^{-5}$ mmHg (less than $10^{-5}$ Torr) is maintained at the jar 12. A gas plate or the like is used as a substrate 15 mounted on one surface of the mounting plate 14 and aligned with respect to the deposition source 13 at an angle $\theta$. As the materials are vaporized by heating the source 13, the vapor emitted will follow a vertical path because a vacuum is maintained inside of the bell jar 12, and is affixed on the base plate 15 at the angle $\theta$ relative to the perpendicular drawn to the upper surface of the substrate 15 (deposition incident angle).

The film thickness d and retardation $\Gamma$ were measured for various deposition incident angles $\theta$ with the use of a tracer type film thickness gauge and a Berek compensator.

The measured values of the deposition incident angle $\theta$ and retardation $\Gamma$ are given in Table 1 below. In the Table, $\Delta n$ denotes the value for $(n_X - n_Y)$ calculated from the film thickness d and retardation $\Gamma$.

TABLE 1

| Deposition incident angle ($\theta°$) | Film thickness ($\times 10^3$ Å) | $\Gamma$ (Å) | $\Delta n$ |
|---|---|---|---|
| 0 | 7.0 | 0 | 0.000 |
| 30 | 7.2 | 109 | 0.015 |
| 45 | 5.0 | 208 | 0.041 |
| 60 | 5.1 | 270 | 0.053 |
| 70 | 4.1 | 253 | 0.062 |
| 75 | 4.0 | 320 | 0.080 |
| 80 | 2.8 | 167 | 0.059 |
| 85 | 2.5 | 72 | 0.029 |

EXAMPLE 2

With the use of the first deposition unit 11, silicon monoxide (SiO) used as deposition source 13 was heated in a tantalum boat as heating means 16 for depositing the material on the glass substrate 15. The values for thickness d of the deposited film and retardation $\Gamma$ were measured for various values of the deposition incident angle $\theta$.

The deposition incident angles $\theta$ and the measured values of the thickness d and retardation $\Gamma$ are shown in Table 2 below.

TABLE 2

| Deposition incident angle ($\theta°$) | Film thickness ($\times 10^3$ Å) | $\Gamma$ (Å) | $\Delta n$ |
|---|---|---|---|
| 0 | 9.0 | 0 | 0.000 |
| 45 | 8.0 | 9 | 0.001 |
| 60 | 9.6 | 120 | 0.013 |
| 75 | 8.0 | 309 | 0.039 |
| 85 | 4.0 | 155 | 0.039 |

EXAMPLE 3

With the use of the first deposition unit 11, silicon monoxide (SiO) used as deposition source 13 was heated in a tantalum boat used as heating means 16 for effecting deposition on the glass substrate 15. The various values for the film thickness d and retardation Γ were measured for a constant deposition incident angle θ of 75° and various temperatures Ts of the glass substrate 15.

The temperatures Ts of the glass substrate 15 and the measured values of the film thickness d and retardation Γ are shown in Table 3 below.

TABLE 3

| Ts (°C.) | Film thickness d(× 10³ Å) | Γ (Å) | Δ n |
|---|---|---|---|
| room temperature | 4.7 | 174 | 0.037 |
| 350 | 4.7 | 155 | 0.033 |
| 460 | 3.8 | 115 | 0.030 |

EXAMPLE 4 with the use of the first deposition unit 11, various dielectric materials used as deposition source 13 were heated by various heating means 16 for effecting deposition on the substrate 15. The values of the film thickness d and retardation Γ were measured for a constant deposition incident angle θ of 75° and various dielectric materials used as deposition source 13.

The dielectric materials and heating means for the deposition source with measured values for the film thickness d and retardation Γ are shown in Table 4. In this Table, Ta denotes a heating means in which the deposition source is accommodated in a tantalum boat to which a heating electric current is supplied, W a heating means in which a basket type tungsten heater coated with alumina (Al₂O₃) is used for heating, and EB a heating means in which an electron beam is used for providng local heating.

TABLE 4

| Dielectric materials | Heating means | Film thickness d(× 10³ Å) | Γ (Å) | Δ n |
|---|---|---|---|---|
| SiO | Ta | 8.0 | 309 | 0.039 |
| Y₂O₃ | EB | 14.0 | 155 | 0.011 |
| TiO₂ | EB | 9.0 | 803 | 0.089 |
| ZrO₂ | EB | 19.0 | 547 | 0.038 |
| CeO₂ | EB | 10.0 | 721 | 0.072 |
| HfO₂ | EB | 5.1 | 223 | 0.044 |
| Al₂O₃ | EB | 6.9 | 270 | 0.039 |
| Ga₂O₃ | EB | 6.0 | 223 | 0.037 |
| Substance-1 | EB | 11.0 | 830 | 0.075 |
| ZnS | W | 6.0 | 80 | 0.013 |

Note:
Substance-1 in the above Table denotes a sintered substance consisting essentially of zirconium oxide (ZrO₂) and zirconium titanate (ZrTiO₄).

EXAMPLE 5

With the use of a second deposition unit 21, titanium dioxide (TiO₂) as a deposition source 23 was deposited with a deposition incident angle of 75°. Thus an octant plate (⅛-wave plate) for the light of the wavelength 5600 Å, that is, a double refraction plate with retardation Γ equal to 700 Å, was obtained.

Figure 4:
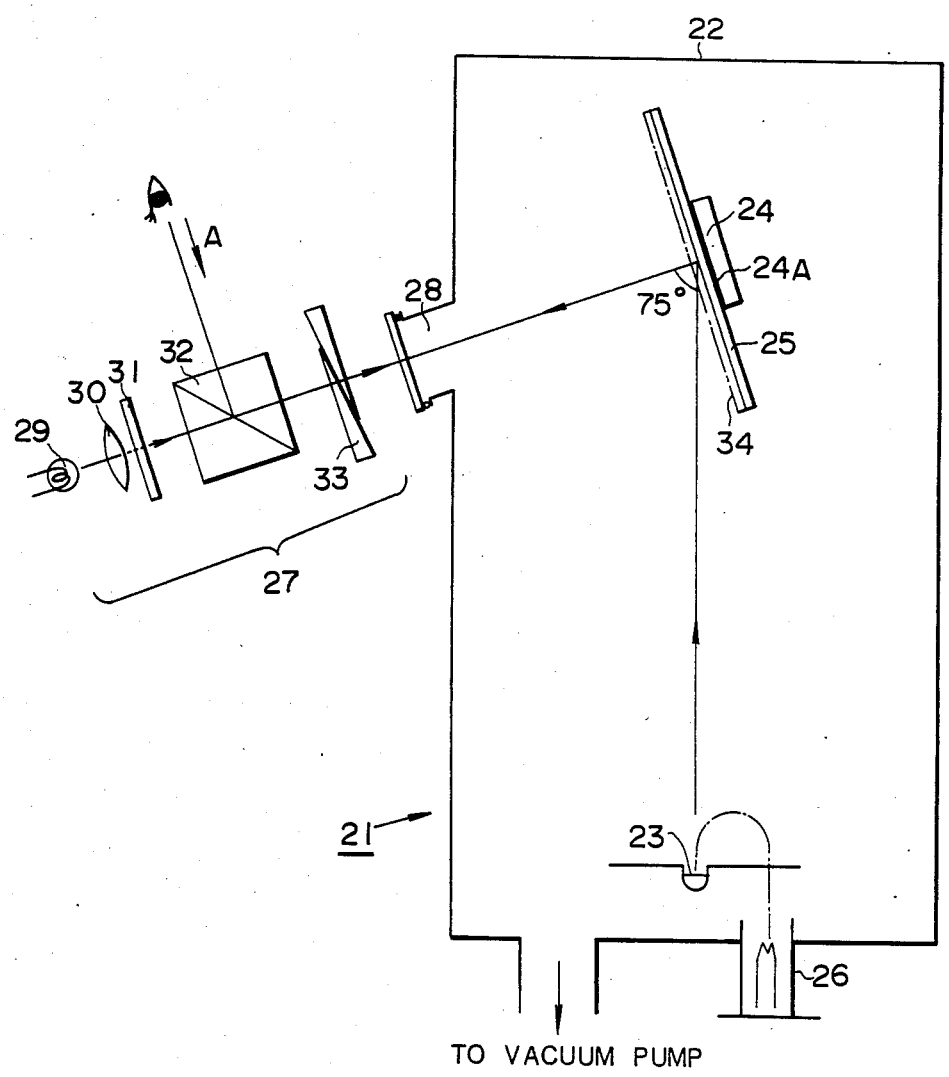
FIG. 4 is a side elevation showing a second deposition unit.

As shown in FIG. 4, the second deposition unit 21 is made up of a bell jar 22 from which air may be exhausted by a vacuum pump, not shown, a deposition source 23 consisting of titanium dioxide, an electron gun 26 adapted for heating the depositiion source, a substrate mounting plate 24 for mounting a glass substrate 25, and a monitor unit 27. The inside of the bell jar 22 is maintained at a pressure less than 10⁻⁵ mmHg by a vacuum pump, not shown. A titanium dioxide deposition source 23 is placed at the lower end of the bell jar 22. An electron gun 26 is placed adjacent to the source and facing upwardly in the drawing. The outgoing electron beam from gun 26 is controlled in the flowing direction by magnets, not shown, and irradiated on the source 23 for heating and vaporizing the source 23. A glass substrate 25 is attached to one side 24A of the mounting plate 24 provided in turn in an upper zone of the bell jar 22. The glass substrate 25 is attached to the plate 24 is secured so that a deposition incident angle is equal to 75°, and acts as a mirror with respect to the light beam coming from the glass substrate 25. An opening 28 aligned with a perpendicular drawn to the glass substrate 25 is bored through the peripheral wall of the bell jar 22. The monitor unit 27 having said perpendicular as its optical axis is placed outside of the monitor window 28 and made up of a light source 29, a collimator lens 30, a band-pass interference filter 31, a polarization beam splitter 32 and a variable phase plate 33.

The inventive method in which the double refraction plate acting, for example, as an octant plate to the light with a wavelength of 5600 Å may be obtained by using the aforementioned second deposition unit 21, is now described below. For producing the octant plate, the bandpass interference filter 31 of the monitor unit 27 is set to a transmission wavelength of 5600 Å, and the variable phase 33 is designed as minus octant plate (−⅛-wave plate). In other words, with the refractive index $n_X$ of the octant plate (⅛-wave plate) in the X-axis direction (a direction perpendicular to the drawing paper of FIG. 4) being larger than the refractive index thereof in the Y-axis direction ($n_X > n_Y$) as in the present embodiment, the refractive index $n_X$ of the variable phase plate 33 in the X-axis direction is less than the refractive index $n_Y$ thereof in the Y-axis direction ($n_X < n_Y$) with the retardation being equal to −700 Å. Thus the minus octant plate is equivalent to the octant plate rotated 90° in one or the other direction about the optical axis. In the present specification, the octant plate (⅛-wave plate) is a double refraction plate having an X-axis component advanced in phase by one-eighth of a wavelength as compared to its Y-axis component. Similarly, the minus octant plate (−⅛-wave plate) is a double refraction plate lagging in phase by one-eight of a wavelength as compared to its Y-axis component.

When the deposited film 34 is not formed on the glass plate 25, the outgoing light from the source 29 of the monitor unit 27 is collimated to a parallel beam by the collimator lens. The light is then filtered by the interference filter 31 so that only the light beam having the wavelength of 5600 Å is passed through the filter. The light thus filtered is split by beam splitter 32 whereby only polarized light a having a specific plane of polarization is passed to the variable phase plate 33. This polarized light a is modulated by variable phase plate 33 by minus one-eighth of the wavelength (thus its X-axis component lagging in phase behind the Y-axis component by one-eighth of the wavelength) and reflected by the mounting plate 24 to be modulated again by the variable phase plate 33 by minus one-eighth of the wavelength to a polarized light b. Therefore, the polarized light b is modulated by minus one quarter wavelength relative to the polarized light a. Hence the reflected polarized light b is reflected in a right-angle direction by the beam splitter 32 thus providing a bright field of sight observed from a direction indicated by the arrow mark A.

As the deposition proceeds and the retardation Γ of the deposited film 34 on the glass substrate 25 is equal to 700 Å, the polarized light a is modulated by minus one-eighth of the wavelength by the variable phase plate 33. The polarized light is passed through the deposited film 34 whereby it is modulated by plus one-eighth of the wavelength and restored to the state of the polarized light a. This polarized light a is reflected by the mounting plate 24 and again passed through the film 34 whereby it is modulated by one-eighth the wavelength and restored to the state of polarized light a. The light is again transmitted through variable phase plate 33 whereby it is modulated by minus one-eighth of the wavelength and restored to the state of the polarized light a. Hence the reflected light has its plane of polarization coincident with that of polarized light and thus may be transmitted through the beam splitter, thus presenting a dark field of sight as viewed from the direction A.

Hence, by using the second deposition unit 21, the deposition process can be observed through the monitor unit 27 and can be terminated when the field of sight is darkest such that the resulting film 34 acts as highly accurate octant plate.

Moreover, in the above Example 5, a variety of wave plates, that is, double refraction plates having optional retardation Γ such as a quarter plate, may be obtained by optionally changing the retardation Γ of the variable phase plate 33.

From the above Examples, it may be contemplated that deposited films aving a certain degree of bi-refringence may be obtained by making use of light transmitting materials such as metal oxides, metal sulfides, metal nitrides, metal halogenides, or high polymeric materials. Above all, double refraction plates having higher retardation Γ may be obtained by using oxides of titanium (Ti), zirconium (Zr), cerium (Ce), galium (Ga), aluminium (Al), or silicon (Si) as a deposition source either singly or in combination. Double refraction plates with higher retardation Γ may be obtained by using titanium dioxide ($TiO_2$).

Although the desired effect may be realized with the deposition incident angle larger than 30°, a deposition incident angle larger than 45° and preferably 75° may be used for increasing the retardation Γ of the double refraction plate.

From the foregoing it will be apparent that, according to the present invention, since the dielectric material is directed obliquely to and deposited on the substrate. Novel double refraction plates of desired size and optional retardation may be produced easily at reduced costs and with improved accuracy.

What is claimed is:

1. A process for manufacturing a double refraction plate, comprising the steps of: impinging and vapor-depositing dielectric material on a surface of a substrate from an oblique direction of at least 30° relative to a perpendicular to a surface thereof; and controlling the impinging oblique direction and deposited film thickness so that a resulting double refraction layer on the surface has a desired retardation of at least one-eighth of a wavelength.

2. The process as claimed in claim 1 characterized by depositing dielectric material at an incident angle more than 45°.

3. The process as claimed in claim 1 characterized by using a material selected from the group consisting of an oxide of titanium (Ti), an oxide of zirconium (Zr), an oxide of cerium (Ce), an oxide of gallium (Ga) and an oxide of silicon (Si) as dielectric material.

4. The process as claimed in claim 1 characterized by using an oxide of titanium (Ti) as dielectric material.

5. A process according to claim 1 wherein a desired retardation is achieved partly through selection of the dielectric material being deposited.

6. A process according to claim 1 wherein the dielectric material is transparent.

7. A process for producing a double refraction plate, comprising the steps of: impinging and depositing dielectric material on a substrate from an oblique direction of at least 30° relative to a perpendicular to the surface thereof so as to create a double-refraction layer on the surface; and directing a polarized light through a variable phase plate to said substrate, said polarized light having a plane of polarization in a specific direction, and by observing the light reflected from said substrate through said variable phase plate determining a retardation of the resulting double refraction plate and controlling the impinging oblique direction and deposited film thickness so as to achieve a desired retardation of at least one-eight of a wavelength.

8. The process as claimed in claim 7 characterized by controlling the retardation to be equal to one-fourth of a wavelength.

9. The process as claimed in claim 7 characterized by controlling the retardation to be equal to one-eighth of a wavelength.

10. A double refraction plate produced by the steps of: impinging and vapor-depositing dielectric material on a surface of a substrate from an oblique direction of at least 30° relative to a perpendicular to the surface thereof; and controlling the impinging oblique direction and deposited film thickness so that a resulting double refraction layer on the surface has a desired retardation of at least one-eighth of a wavelength.

11. The double refraction plate as claimed in claim 10 having a deposited film providing a retardation equal to one-fourth of a wavelength.

12. The double refraction plate as claimed in claim 10 having a deposited film providing a retardation equal to one-eighth of a wavelength.

13. A process for manufacturing a double refraction plate, comprising the steps of:
    selecting a transparent dielectric material;
    vapor-depositing the dielectric material on a surface of a substrate at a given angle of at least 30° relative to a perpendicular to the surface;
    observing a retardation of a deposited double refraction layer on the substrate during the overall process; and
    controlling the retardation so as to achieve a desired retardation value of at least one-eighth of a wave length by controlling the angle of incidence of deposited material and thickness of deposited material.

* * * * *